US011278553B2

(12) United States Patent
Rabovsky et al.

(10) Patent No.: US 11,278,553 B2
(45) Date of Patent: Mar. 22, 2022

(54) DIETARY SUPPLEMENT COMPOSITIONS FOR CARDIOVASCULAR HEALTH

(71) Applicant: Melaleuca, Inc., Idaho Falls, ID (US)

(72) Inventors: Alexander B. Rabovsky, Idaho Falls, ID (US); Jeremy Ivie, Ammon, ID (US)

(73) Assignee: Melaleuca, Inc., Idaho Falls, ID (US)

( * ) Notice: Subject to any disclaimer, the term of this patent is extended or adjusted under 35 U.S.C. 154(b) by 0 days.

(21) Appl. No.: 15/395,105

(22) Filed: Dec. 30, 2016

(65) Prior Publication Data

US 2017/0209463 A1 Jul. 27, 2017

Related U.S. Application Data

(63) Continuation of application No. 12/854,944, filed on Aug. 12, 2010, now abandoned.

(60) Provisional application No. 61/233,242, filed on Aug. 12, 2009.

(51) Int. Cl.
| | |
|---|---|
| A61K 31/575 | (2006.01) |
| A23L 33/11 | (2016.01) |
| A23L 33/12 | (2016.01) |
| A61K 9/48 | (2006.01) |
| A61K 31/122 | (2006.01) |
| A61K 31/202 | (2006.01) |
| A61K 38/48 | (2006.01) |
| A61K 31/385 | (2006.01) |
| A23L 33/10 | (2016.01) |
| A61K 31/232 | (2006.01) |
| A23L 33/105 | (2016.01) |
| A61K 9/00 | (2006.01) |
| A61K 9/20 | (2006.01) |

(52) U.S. Cl.
CPC ............ *A61K 31/575* (2013.01); *A23L 33/10* (2016.08); *A23L 33/105* (2016.08); *A23L 33/11* (2016.08); *A23L 33/12* (2016.08); *A61K 9/0053* (2013.01); *A61K 9/20* (2013.01); *A61K 9/48* (2013.01); *A61K 9/4825* (2013.01); *A61K 31/122* (2013.01); *A61K 31/202* (2013.01); *A61K 31/232* (2013.01); *A61K 31/385* (2013.01); *A61K 38/4873* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 4,576,284 A | 3/1986 | Wittwer et al. | |
| 4,897,224 A | 1/1990 | Kondo et al. | |
| 5,502,045 A | 3/1996 | Miettinen et al. | |
| 6,087,353 A | 7/2000 | Stewart et al. | |
| 6,211,206 B1 | 4/2001 | Ikeda et al. | |
| 6,333,047 B1 | 12/2001 | Katagihara et al. | |
| 6,933,291 B2 | 8/2005 | Qi et al. | |
| 7,229,651 B2 | 6/2007 | Perkes | |
| 2003/0203854 A1 | 10/2003 | Pischel et al. | |
| 2005/0032757 A1* | 2/2005 | Cho | A23L 33/12 514/170 |
| 2009/0110674 A1 | 4/2009 | Loizou | |

FOREIGN PATENT DOCUMENTS

WO   WO 2000/04887   2/2000

OTHER PUBLICATIONS

Sabharwal (Molecular and Cellular Biochemistry 2008, vol. 306 125-132).*
Traber ("Vitamin E, Antioxidant and Nothing More" Free Radical Biology Medicine, 2007 43(1) 4-15) (Year: 2007).*
Yoshida ("Antioxidant Effects of Phytosterol and Its Components' Journal of Nutritional Science and Vitaminology", 2003, 49(4) 277-280, Abstract provided). (Year: 2003).*
U.S. Appl. No. 10/913,848, filed Aug. 6, 2004, 20050032757, Feb. 10, 2005, Cho.
"Certificate of Analysis," Bromelain 2500 GDU, Hong Mao Biochemicals Co., Ltd., Apr. 26, 2002, 1 page.
"Certificate of Analysis," Fish Blend 18:12TG, Bioriginal Food & Sciences Corp., Jan. 10, 2003, 1 page.
"Certificate of Analysis," Fish Oil 18/12, Berg Lipidtech AB, Feb. 13, 2002, 1 page.
"Certificate of Analysis," Fish Oil 18/12, Clover Corporation, Jun. 30, 2001, 1 page.
"Certificate of Analysis," Fish Oil 1812 TG, Denofa Leknes, Mar. 1, 2002, 1 page.
"Certificate of Analysis," Fish Oil 30/20, Berg Lipidtech AB, Jun. 18, 2001, 1 page.
"Certificate of Analysis," Soya Lecithin, Riceland Foods, Inc., Jan. 6, 2003, 1 page.
"Certificate of Analysis," Ubidecarenone "MGCC" (Coenzyme Q10), Mitsubishi Gas Chemical Company, Inc., Dec. 26, 2002, 1 page.
"Certificate of Analysis," Vegapure 67WDP, Cognis Corporation, Mar. 24, 2003, 1 page.
"Certificate of Analysis," Vegapure 95, Cognis Corporation, May 31, 2002, 1 page.
"Certificate of Quality," Soybean Salad, Bunge Foods, 2002, 1 page.
Alaswad et al., "Combination drug therapy for dyslipidemia," *Curr. Atheroscler, Rep.*, 1999, 1(1):44-49.
Bourque et al., "Consumption of an Oil Composed of Medium Chain Triacylgycerols, Phytosterols, and N-3 Fatty Acids Improves Cardiovascular Risk Profile in Overweight Women," *Metabolism*, 2003, 52(6):771-777.
Choi et al., "Effect of dietary n-3 polyunsaturated fatty acids on cholesterol synthesis and degradation in rats of different ages," *Lipids*, 1989, 24(1):45-50.

(Continued)

Primary Examiner — Robert J Yamasaki
Assistant Examiner — Charles Zoltan Constantine
(74) Attorney, Agent, or Firm — Fish & Richardson P.C.

(57) ABSTRACT

This document provides dietary supplements. For example, composition having a combination of ingredients useful in reducing cholesterol and improving overall cardiovascular health as well as methods for reducing cholesterol and improving overall cardiovascular health are provided.

16 Claims, No Drawings

(56) References Cited

OTHER PUBLICATIONS

Coro Wise™ Phytosterols, Product Information Sheet, Cargill, date unknown, 1 page.
CoroWise™ Phytosterol Esters, Product Information Sheet, Cargill, date unknown, 1 page.
Ewart et al., "Fish Oil Containing Phytosterol Esters Alters Blood Lipid Profiles and Left Ventricle Generation of Thromboxane A2 in Adult Guinea Pigs," *J. Nutr.*, 2002, 132(6):1149-1152.
Falbe; Surfactants in Consumer Products Theory, Technology and Application; 1987; pp. 149-153; Springer-Verlag; Germany.
Fish Oil 1812 TG, Product Information Sheet, Denofa Leknes, date unknown, 1 page.
Hazell and Johnson, "In vitro estimation of iron availability from a range of plant foods: influence of phytate, ascorbate and citrate,"*British J. Nutr.*, vol. 57, No. 2, (Mar. 1987) pp. 223-233.
Johnson, "What can in vitro methods tell US about mineral availability?" *Biol. Trace Element Research*, vol. 19, No. 1-2 (Jan.-Feb. 1989), pp. 3-10.
Kaitaranta, "Control of Lipid Oxidation in Fish Oil with Various Antioxidative Compounds," JAOCS (Aug. 1992) vol. 69, No. 8, pp. 810-813.
Kelly, "Bromelain: A Literature Review and Discussion of its Therapeutic Applications," http://www.thore.com/altmedrev/fulitext/bromelain1-4.html, printed from the internet on Mar. 11, 2003, 16 pages.
Kurowska, "Determination of cholesterol-lowering potential of minor dietary components by measuring apolipoprotein B responses inHepG2 cells" *Methods in Enzymology*, vol. 335, (2001), pp. 398-404.
Material Specification, Vegapure 67WDP, Cognis Corporation, Sep. 25, 2002, 1 page.
Melaleuca, Phytomega FAQ, "Phytomega Heart Health Supplement", Melaleuca, (2008) available online at cdnus.melaleuca.com/POF/BusinessCenter/Reference_Library/PIB/FAQ_Phytomega_enUs.pdf.
Miller et al., "An in vitro method for estimation of iron availability from meals," *Amer. J. Clinical Nutr.*, vol. 34, No. 10 (Oct. 1981), pp. 2248-2256.
Monograph-Bromelain, http://www.thome.com/ahmedrev/brom3-4.html printed from the internet on Mar. 11, 2003, 6 pages.
Motzok et al., "Bioavailability, in vitro solubility, and physical and chemical properties of elemental iron powders," *J. Assoc. Anal. Chem.*, vol. 61, No. 4 (Jul. 1978), pp. 887-893.
Oomen et al., "Comparison of five in vitro digestion models to study the bioaccessibility of soil contaminants," *Environ. Sci. Tech.*, vol. 36, No. 15 (Aug. 1, 2002), pp. 3326-3334.
Phytosterol Esters (Plant Sterol and Stanol Esters), Institute of Food Science & Technology (UK), http://www.ifst.org/botttop29.htm, printed from the internet on Mar. 11, 2003, 11 pages.
Phytosterols ADM product code 040095, Archer Daniels Midland Company, date unknown, 1 page.
Powell et al., "In vitro mineral availability from digested tea: a rich dietary source of managanese ," *Analyst*, vol. 123, No. 8 (Aug. 1998), pp. 1721-1724.
Product Sheet EPAX 3000 TG, Pronova Biocare, date unknown, 3 pages.
Rao et al., "An in vitro method for predicting the bioavailability of iron from foods," Am J Clin Nutr, vol. 31, (Jan. 1978) pp. 169-175.
Russell et al., "Improvement of vascular dysfunction and blood lipids of insulin-resistant rats by a marine oil-based phytosterol compound," *Lipids*, vol. 37, No. 2 (Feb. 2002), pp. 147-152.
Sabharwal et al., "Alpha-Lipoic acid and ascorbate prevent LDL oxidation and oxidant stress in endothelial cells" Molecular and Cellular Biochemistiy, 2008, vol. 306 pp. 125-132.
Shanmuganayagam and Folts, "Effect of polyphenolic flavonoid compounds on platelets," *Methods in Enzymology*, vol. 335, (2001), pp. 369-380.
Specifications & Certificate of Analysis—Omegafish Oil (DHA 50%), NutriScience Innovations, LLC., Nov. 2002, 2 pages.
Specifications & Certificate of Analysis—Omegafish Oil 45% (Triglyceride Form), NutriScience Innovations, LLC., Jan. 2, 2003, 1 page.
Specifications—Omegafish Oil (DHA 50%), NutriScience Innovations, LLC., Jun. 2003, 1 page.
Specifications—Omegafish Oil 50 % (EPA 30%/DHA 20%), NutriScience Innovations, LLC., Nov. 2002, 1 page.
Technical Bulletin Dry n-3® 18:12 Omega-3 Fatty Acids, BASF Corporation, 2001, 1 page.
Technical Bulletin Dry n-3® 5:25 Omega-3 Fatty Acids, BASF Corporation, 2001, 1 page.
Teichert et al., "Plasma kinetics, metabolism, and urinary excretion of alpha-lipoic acid following oral administration in healthy volunteers," J. Clin. Pharmacol., 43:1257-1267.
Vegapure™ 95 (Vegetable Sterol Esters), Product Data Sheet, Cognis Corporation, Oct. 18, 2002, 2 pages.
Vendor Certificate/Certificate of Analysis—Refined Phytosterol Ester (ES 010 p. 04), Loders Croklaan Lipid Nutrition, Dec. 12, 2002, 1 page.
Vitality for life, "Phytomega" (2003), USA, available at content.melaleuca.com/wc/pdf/Phytomega_lnfo.pdf.
What are Phytosterols? Forbes Medi-Tech Inc., http://www.forbesmedi.com/s/Phytosterols.Asp, printed from the internet on Mar. 11, 2003, 2 pages.
Wrobel et al., "Studies on bioavailability of some bulk and trace elements in Mexican tortilla using an in vitro model," *Biol. Trace Element Research*, vol. 68, No. 2 (May 1999), pp. 97-106.

\* cited by examiner

DIETARY SUPPLEMENT COMPOSITIONS FOR CARDIOVASCULAR HEALTH

CROSS-REFERENCE TO RELATED APPLICATIONS

This application is a Continuation of, and claims the benefit of priority under 35 U.S.C. § 120 to, U.S. application Ser. No. 12/854,944 filed on Aug. 12, 2010, which claims priority under 35 U.S.C. § 119(e) to U.S. Provisional Application Ser. No. 61/233,242, filed on Aug. 12, 2009, which is incorporated by reference in its entirety herein.

BACKGROUND

1. Technical Field

This document relates to the field of dietary supplements. For example, this document relates to composition having a combination of ingredients useful in reducing cholesterol and improving overall cardiovascular health.

2. Background Information

Cardiovascular disease (CVD) is a major cause of deaths and disabilities throughout the world. The risk of CVD is determined by several factors, such as a person's lifestyle, diet, and genetic background. While physicians have used various statin drugs, such as lovastatin, pravastatin, and simvastatin to reduce cholesterol levels, the impact of these prescription medications on the heart, liver, and muscles have raised safety concerns. In addition, the use of statins is mainly focused on reducing serum cholesterol levels, while CVD has multiple pathological mechanisms.

A major factor in CVD is atherosclerosis, a process of accumulating plaques in major blood vessels. This disease is very hard to treat and almost impossible to reverse, but it is highly preventable. There are few risk factors responsible for atherosclerosis progression. One of the most important is high blood cholesterol. According to modern research the mechanism of arterial plaque formation includes free radical oxidation of LDL, the major cholesterol transporting complex in the blood. Another important aspect of atherosclerosis development is inflammation. Increased inflammatory background is not just a risk factor, it is an indicator of active plaque formation processes. Thus, a high level of inflammatory markers in the blood is believed to be a better predictor of cardiac events than high cholesterol.

Given the grave consequences of CVD and the costs and risk associated with medical treatments, there is a need for nutritional interventions that are useful for preventing the occurrence and reoccurrence of these conditions.

SUMMARY

This document provides dietary supplements. For example, this document provides composition having a combination of ingredients useful in reducing cholesterol and improving overall cardiovascular health as well as methods for reducing cholesterol and improving overall cardiovascular health.

One aspect of this document features a dietary supplement comprising, or consisting essentially of, (a) from about 400 mg to about 3000 mg phytosterols, (b) from about 110 mg to about 1000 mg omega-3 fatty acids, (c) from about 6 mg to about 60 mg coenzyme Q-10, (d) from about 6 mg to about 45 mg alpha lipoic acid, and (e) from about 2.5 mg to about 20 mg bromelain. In some cases, the dietary supplement can comprise, or consist essentially of, (a) from about 1400 mg to about 2800 mg phytosterols, (b) from about 300 mg to about 800 mg omega-3 fatty acids, (c) from about 20 mg to about 40 mg coenzyme Q-10, (d) from about 20 mg to about 36 mg alpha lipoic acid, and (e) from about 8 mg to about 15 mg bromelain. In some cases, the dietary supplement can comprise, or consist essentially of, (a) about 2000 mg phytosterols, (b) about 550 mg omega-3 fatty acids, (c) about 30 mg coenzyme Q-10, and (d) about 30 mg alpha lipoic acid.

In some cases, a dietary supplement can comprise, or consist essentially of, (a) about 500 mg phytosterols; (b) about 250 mg omega-3 fatty acids; (c) about 7.5 mg coenzyme Q-10; and (d) about 7.5 mg alpha lipoic acid. In some cases, a dietary supplement can comprise, or consist essentially of, (a) from about 1000 mg to about 3000 mg phytosterols; (b) from about 500 mg to about 1500 mg omega-3 fatty acids; (c) from about 15 mg to about 45 mg coenzyme Q-10; (d) from about 15 mg to about 45 mg alpha lipoic acid; and (e) from about 2.5 mg to about 20 mg bromelain.

Further provided herein is a method for improving cardiovascular heath in a mammal. In some cases, the method can include administering to the mammal a daily dosage of a dietary supplement, wherein the dietary supplement can include: (a) from about 1000 mg to about 3000 mg phytosterols; (b) from about 500 mg to about 1500 mg omega-3 fatty acids; (c) from about 15 mg to about 45 mg coenzyme Q-10; (d) from about 15 mg to about 45 mg alpha lipoic acid; and (e) from about 2.5 mg to about 20 mg bromelain.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

In the following description, numerous specific details are set forth in order to provide a thorough understanding of the present document. It will be obvious, however, to one skilled in the art that the subject matter provided herein may be practiced without these specific details. In other instances, well-known aspects of dietary supplements and the various compositions discussed herein have not been described in particular detail in order to avoid unnecessarily obscuring the subject matter provided herein.

This document provides methods and compositions related to lowering blood cholesterol, reducing the inflammation background, and increasing the antioxidant potential of the blood. The methods and compositions are believed to slow down atherosclerosis development and lower the risk of cardiac events. In particular, the methods and compositions are believed to provide a variety of health benefits, including: helping reduce the risk of heart disease, helping support heart and blood vessel function, naturally helping reduce cholesterol levels for a healthier heart and life, supporting blood circulation, adding coenzyme Q-10 to offset reduced amounts during aging, and helping to regenerate antioxidants.

For example, the document provides compositions (e.g. dietary supplements) containing a sterol compound, omega-3 fatty acids (EPA/DHA), coenzyme Q10, and α-lipoic acid.

Also provided herein are methods of administering a daily dose of a dietary supplement as provided herein. In some cases, the dietary supplement can be formulated with amounts as provided herein. Administration can be provided as one or more compositions (e.g., tablets).

Sterol Compounds

Compositions provided herein can contain a sterol compound such as a phytosterol compound. In some cases, the sterol can be synthetic. The term "sterol" includes, without limitation, plant, animal, and synthetic sterols, sterol esters, stanols, and stanol esters. Plant sterols (and sterol esters) are naturally occurring substances present in the diet as minor components of vegetable oils, while plant stanols (and stanol esters) are hydrogenation compounds of the plant sterols.

The cholesterol lowering effect of sterols is thought to be associated with their structural similarity.

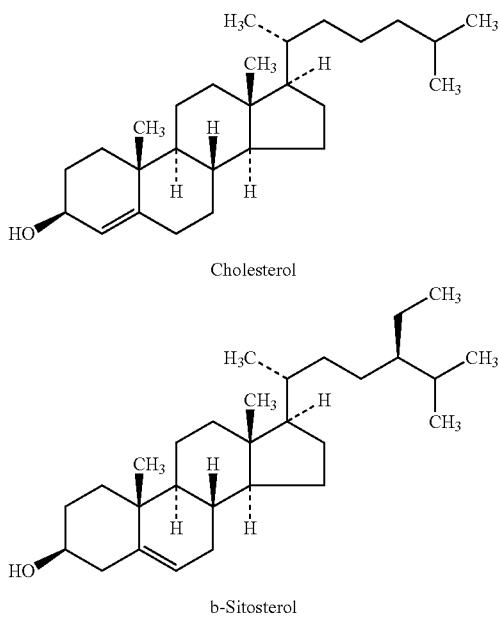

Sterols may compete with cholesterol for places in micelles—small fat particles which form during digestion in order to adsorb fat. Because of this, sterols may prevent absorption and re-absorption of cholesterol from the intestinal tract and thus can affect blood cholesterol levels.

Sterols have been approved for safe use by the FDA and they have been safely used in studies lasting up to 18 months. A significant number of research studies have shown that sterols can reduce total cholesterol and LDL cholesterol levels.

Sterol compounds (e.g., phytosterols and phytosterol esters) can be obtained commercially from a variety of sources, e.g., Cargill, Inc. (Minneapolis, Minn.), Loders and Croklaan (Channahon, Ill.), Cognis Nutrition and Health (La Grange, Ill.), Forbes Meditech (Vancouver, B.C. Canada), and ADM (Decatur, Ill.) and can demonstrate a range of sterol profiles. In addition, sterol compounds can be synthesized and/or obtained from natural sources such as soy oil, canola oil, or wheat germ oil as described elsewhere (see e.g. U.S. Pat. Nos. 6,411,206; 5,502,045; 6,087,353; and 4,897,224, each of which is incorporated herein by reference in its entirety).

Suitable examples of phytosterol esters that can be used to prepare a composition provided herein include, without limitation, beta-sitosterol laurate ester, alpha-sitosterol laurate ester, gamma-sitosterol laurate ester, campesterol myristearate ester, stigmasterol oleate ester, campesterol stearate ester, beta-sitosterol oleate ester, beta-sitosterol palmitate ester, beta-sitosterol linoleate ester, alpha-sitosterol oleate ester, gamma-sitosterol oleate ester, beta-sitosterol myristearate ester, beta-sitosterol ricinoleate ester, campesterol laurate ester, campesterol ricinoleate ester, campesterol oleate ester, campesterol linoleate ester, stigmasterol linoleate ester, stigmasterol laurate ester, stigmasterol caprate ester, alpha-sitosterol stearate ester, gamma-sitosterol stearate ester, alpha-sitosterol myristearate ester, gamma-sitosterol palmitate ester, campesterol ricinoleate ester, stigmasterol ricinoleate ester, campesterol ricinoleate ester, beta-sitosterol, alpha-sitosterol, gamma-sitosterol, campesterol, stigmasterol, and stigmasterol stearate ester.

In some embodiments, a sterol compound can be a phytostanol ester. Sterol compounds such as phytostanols and phytostanol esters can be obtained commercially from, e.g., Forbes Meditech (Vancouver, B.C. Canada), or can be readily synthesized. Alternatively, phytostanols and phytostanol esters can be obtained from natural sources such as soy oil, canola oil, or wheat germ oil as described elsewhere (see e.g. U.S. Pat. Nos. 6,411,206; 5,502,045; 6,087,353; and 4,897,224).

Examples of phytostanol esters that can be used to make a composition provided herein include, without limitation, beta-sitostanol laurate ester, campestanol myristearate ester, stigmastanol oleate ester, campestanol stearate ester, beta-sitostanol oleate ester, beta-sitostanol palmitate ester, beta-sitostanol linoleate ester, beta-sitostanol myristearate ester, beta-sitostanol ricinoleate ester, campestanol laurate ester, campestanol ricinoleate ester, campestanol oleate ester, campestanol linoleate ester, stigmastanol linoleate ester, stigmastanol laurate ester, stigmastanol caprate ester, stigmastanol stearate ester, alpha-sitostanol laurate ester, gamma-sitostanol laurate ester, alpha-sitostanol oleate ester, gamma-sitostanol oleate ester, alpha-sitostanol stearate ester, gamma-sitostanol stearate ester, alpha-sitostanol myristearate ester, gamma-sitostanol palmitate ester, campestanol ricinoleate ester, stigmastanol ricinoleate ester, campestanol ricinoleate ester, beta-sitostanol, alpha-sitostanol, gamma-sitostanol, campestanol, and stigmastanol.

A composition provided herein can contain any type of sterol compound such as a phytosterol, phytosterol ester, phytostanol, or phytostanol ester. In addition, a composition provided herein can contain any amount of sterol compounds (e.g., 10, 25, 50, 100, 200, 250, 300, 325, 350, 375, 400, 425, 450, 475, 500, 525, 550, 575, 600, 625, 650, 675, 700, 750, 800, or 900 mg). For example, between 35 to 95 percent (e.g., from 35 to 95 percent, from 50 to 95 percent, from 75 to 95 percent, from 85 to 95 percent, from 35 to 85 percent, from 35 to 75 percent, or from 35 to 55 percent) of a composition provided herein can contain sterol compounds. In some cases, a composition provided herein can be designed to contain multiple sterol compounds in any relative ratio (e.g., 1:1, 2:1, 3:1, 4:1, 5:1, 6:1, 7:1, 8:1, 9:1, or 10:1). In certain cases, a composition provided herein can be a nutritional supplement with a label indicating that a suggested serving size includes greater than 1 g (e.g., about 1.1, 1.2, 1.3, 1.4, 1.5, 1.6, 1.7, 1.8, 1.9, 2.0, 2.1, 2.2, 2.3, 2.4, 2.5, 2.6, 3.0, 3.5 g or more) of total sterol compounds per day.

Typically, a composition provided herein can be designed to contain a phytosterol ester compound or mixtures thereof. In some cases, a composition provided herein can be designed to contain one or more phytosterol ester compounds in a total amount ranging from about 45% to about 95% by weight of the composition. In certain embodiments, one or more phytosterol ester compounds can be provided in a total amount from about 45% to about 60% by weight of the composition. In other embodiments, one or more phytosterol ester compounds can be provided in a total amount of about 70% to about 85% by weight of the composition.

A composition provided herein can contain one or more phytosterol compounds. In certain embodiments, one or more phytosterols can be present in a total amount from about 1% to about 85% by weight of the composition. In certain compositions, one or more phytosterol compounds may be present in a total amount from about 1% to about 10% by weight of the composition. In other compositions, one or more phytosterols can be present in a total amount of from about 40% to about 55%, or from about 70% to about 85% by weight of the composition.

In certain embodiments, a composition provided herein can contain one or more phytostanol ester compounds, e.g., in a total amount of from about 45% to about 95% by weight of the composition. In certain embodiments, one or more phytostanol ester compounds can be provided in a total amount of about 45% to about 60% by weight of the composition. In other embodiments, one or more phytostanol ester compounds can be provided in a total amount of about 70% to about 85% by weight of the composition.

In certain compositions, one or more phytostanol compounds can be present in a total amount from about 1% to about 85% by weight of the composition. In other compositions, one or more phytostanols can be present in a total amount of from about 1% to about 10%, from about 40% to about 55%, or from about 70% to about 85% by weight of the composition.

Fatty Acid Compounds

The compositions provided herein can contain one or more fatty acid compounds (e.g., ω-3 fatty acid compounds). Omega-3 fatty acids stimulate blood circulation, increase the breakdown of fibrin, a compound involved in clot and scar formation, and additionally have been shown to reduce blood pressure. There is strong scientific evidence that ω-3 fatty acids reduce blood triglyceride levels and regular intake reduces the risk of secondary and primary heart attack.

Two common forms of omega-3 fatty acids are can generally be in a form generally known as eicosapentaenoic acid (EPA) and derivatives thereof and docosahexaenoic acid (DHA) and derivatives thereof.

Fatty acid compounds such as ω-3 fatty acid compounds can be obtained from fish oils or vegetable oils, or synthesized. In some cases, fatty acid compounds such as ω-3 fatty acid compounds can be formulated in a composition as a fish oil or vegetable oil or mixture thereof. For example, a fish oil containing DHA, EPA, or both, can be used to make a composition provided herein. Fish oils are available commercially from BLT Berg Lipidtech AS, Clover Corporation, Denofa AS, Bioriginal Food and Science Corp., ProNova Biocare, BASF, and NutriScience Innovations LLC, and can demonstrate a range of ω-3 fatty acid profiles. In certain cases, a fish oil can contain about 11-14% DHA and about 16-19% EPA, and a total ω-3 fatty acid content of about 33-41%. For example, a fish oil can contain about 12% DHA and about 18% EPA. In other cases, a fish oil can contain about 30-33% EPA and about 20-22% DHA, and a total α-3 fatty acid content of about 50-67%. In other cases, a fish oil can contain about 50-55% DHA and about 5-10% EPA. In yet other cases, a fish oil can contain about 50-55% EPA and about 5-10% DHA. In other examples, a fish oil can contain at least 20% DHA and at least 25% EPA, and a total ω-3 fatty acid content of at least 60%, e.g., at least 65%. In yet other cases, a fish oil can contain about 5% EPA and about 25% DHA, and a total ω-3 fatty acid content of about 30%, e.g., about 35%.

In addition to the use of a pure fish oil, a fish oil containing EPA and/or DHA (or derivatives thereof) can be modified by, e.g., the addition of purified EPA and/or DHA (or derivatives thereof) to result in a particular ratio or amount of EPA and/or DHA (or derivatives thereof). In other embodiments, purified EPA and/or DHA, or derivatives thereof, can be used to make a composition provided herein. In certain embodiments, a ratio of EPA to DHA, or derivatives thereof, can be from about 1:5 to about 5:1, or from about 1:2 to about 2:1, or from about 1.5:1 to about 1:1.5. For example, a fish oil can contain EPA and DHA at a ratio of about 1.5:1.

Typically, a composition provided herein can contain a fish oil in a range of from about 10% to about 55% by weight of the composition, or from about 10% to about 30% by weight of the composition. In other embodiments, EPA and/or DHA, or derivatives thereof, can be used in purified form to make a composition provided herein. The combined amount of EPA and DHA (or derivatives thereof) can range from about 30% to about 55% by weight of the composition. In certain embodiments, the combined amount of EPA and DHA can range from about 20% to about 40% by weight of the composition. In other embodiments, the combined amount of EPA and DHA can range from about 12% to about 16% by weight of the composition.

Fish oils, purified EPA, DHA, and derivatives thereof such as DHA and EPA, can be obtained commercially from, for example, Croda, Inc. (Parsippany, N.J.), Roche Vitamins Ltd. (Parsippany, N.J.), Martek (Boulder, Colo.), Maritex (Sortland, Norway), Seven Seas, Pronova (Lysker, Norway), and Loder Croklann Lipid Nutrition (Channahon, Ill.), and Cargill, Inc. (Minneapolis, Minn.).

A composition provided herein can be a nutritional supplement. A nutritional supplement can include a label indicating that a suggested serving size includes at least 300 mg (e.g., about 300, 350, 400, 420, 450, 500, 500-600, 600-900, 1000, 1100, 1200, 900-1200, 1200-1500 mg, 1500 mg-2 g, 2 g-2.5 g, 2.5 g-3 g, or more) of total ω-3 fatty acids per day. One or more ω-3 fatty acids can be derived from one or more fish, purified ω-3 fatty acids, or mixtures thereof. In some embodiments, a nutritional supplement can include a label indicating that a suggested serving size includes at least 300 mg of DHA and EPA per day.

Coenzyme $Q_{10}$

The compositions provided herein can contain Coenzyme Q-10. Coenzyme Q-10 (also referred to herein as CoQ10), a powerful antioxidant, helps support heart and blood vessel functions and is involved in the process that produces cellular energy. All risk groups (of atherosclerosis) should preferably maintain a healthy blood level of CoQ10. This is important for people who are on statin (inhibitors of cholesterol biosynthesis) therapy.

Coenzyme Q10 (CoQ10) is produced by the human body and is necessary for the basic functioning of cells. CoQ10 plays a key role in producing energy in the mitochondria, the part of a cell responsible for the production of energy in the form of ATP. It does so through the conversion of oxidized and reduced forms (ubiquinone-ubiquinol) of the coenzyme.

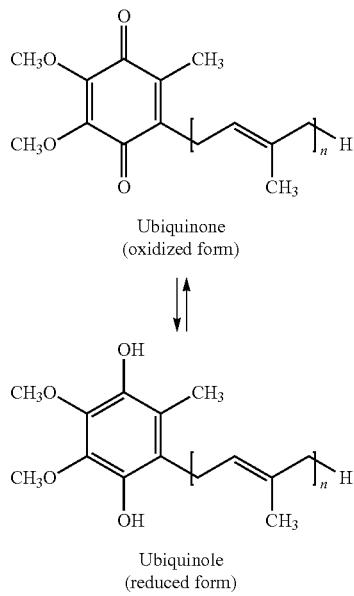

Ubiquinone (oxidized form)

Ubiquinole (reduced form)

The similar transformation play a very important antioxidant role: the major fat soluble, membrane antioxidant vitamin E is only effective in the presence of CoQ10 because of its cyclic regeneration.

CoQ10 levels are reported to decrease with age and to be low in patients with some chronic diseases such as heart conditions, muscular dystrophies, Parkinson's disease, cancer, diabetes, and HIV/AIDS. People with heart failure have been found to have lower levels of CoQ10 in heart muscle cells. Some prescription drugs may also lower CoQ10 levels.

CoQ10 (in appropriate form) is relatively bioavailable. The average plasma level in human is about 0.7-0.9 µg/mL. Desirable levels for people with elevated risk of heart disease is more than 1 µg/mL. Supplementation may increase the plasma level very quickly.

CoQ10 can be included in an amount ranging from about 0.01% to about 2% by weight of the composition, or from about 0.1% to about 1% by weight.

α-Lipoic Acid

The compositions provided herein can contain α-Lipoic acid (LA), also known as thioctic acid, LA is an essential cofactor for several important enzyme complexes, it can directly scavenge (neutralize) physiologically relevant Reactive Oxygen and Nitrogen Species (ROS and RNS), it also can directly or indirectly regenerate the oxidized forms of other antioxidants such as Ascorbic acid, α-Tocopherol, and CoQ10.

LA is a naturally occurring compound that is synthesized in small amounts by plants and animals, including humans. LA contains two thiol (sulfur) groups. The reduced form is known as dihydrolipoic acid (DHLA), while the oxidized form is known as LA.

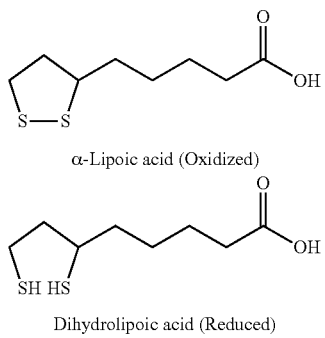

α-Lipoic acid (Oxidized)

Dihydrolipoic acid (Reduced)

Reactive oxygen species (ROS) and reactive nitrogen species (RNS) are highly reactive compounds with the potential to damage DNA, proteins and lipids (fats) in cell membranes. Both LA and DHLA can directly scavenge (neutralize) physiologically relevant ROS and RNS in the test tube. However, it is not clear whether LA acts directly to scavenge ROS and RNS in vivo. When an antioxidant scavenges a free radical, it becomes oxidized itself and is not able to scavenge additional ROS or RNS until it has been reduced. DHLA is a potent reducing agent with the capacity to reduce the oxidized forms of several important antioxidants, including vitamin C and glutathione. DHLA may also reduce the oxidized form of alpha-tocopherol (the alpha-tocopheroxyl radical) directly or indirectly, by reducing the oxidized form of vitamin C (dehydroascorbate), which is able to reduce the alpha-tocopheroxyl radical. Coenzyme Q10 is an important component of the mitochondrial electron transport chain that also has antioxidant activity. DHLA can also reduce oxidized forms of coenzyme Q10, which may also reduce the alpha-tocopheroxyl radical. Although DHLA has been found to regenerate oxidized antioxidants in the test tube, it is not known whether DHLA effectively regenerates other antioxidants under physiological conditions.

In addition to antioxidant regeneration functions, LA has multiple health benefits. Glutathione is an important intracellular antioxidant that also plays a role in the detoxification and elimination of potential carcinogens and toxins. LA has been found to increase glutathione synthesis in cultured cells and in the tissues of aged animals fed LA.

Bromelain

Compositions provided herein can contain bromelain. Generally, the bromelain is provided in an amount ranging from about 0.1% to about 5% by weight of the composition, or from about 0.5% to about 2.5% by weight of the composition. Bromelain is the generic name for a family of sulfhydryl-containing proteolytic enzymes obtained from the pineapple plant. A bromelain enzyme blend generally contains a sulfydryl proteolytic fraction, a peroxidase, an acid phosphatase, several protease inhibitors, and calcium.

Compositions

This document provides compositions that can include one or more of: sterols, omega-3 fatty acids, coenzyme Q-10, and alpha lipoic acid. In some cases, a dietary supplement composition provided herein can contain the amounts indicated in Table 1 below.

TABLE 1

| Component | Daily Dosage |
|---|---|
| Phytosterols | 2000 mg |
| Omega-3 fatty acids | 550 mg |

TABLE 1-continued

| Component | Daily Dosage |
| --- | --- |
| Coenzyme Q-10 | 30 mg |
| Alpha lipoic acid | 30 mg |

In some cases, a dietary supplement composition provided herein can contain the amounts indicated in Table 2 below.

TABLE 2

| Component | Daily Dosage |
| --- | --- |
| Phytosterols | 2000 mg |
| Omega-3 fatty acids | 1000 mg |
| Coenzyme Q-10 | 30 mg |
| Alpha lipoic acid | 30 mg |

In another case, a daily dosage of the dietary supplement composition can contain the following:
  a) from about 400 mg to about 3000 mg phytosterols
  b) from about 110 mg to about 1000 mg omega-3 fatty acids;
  c) from about 6 mg to about 60 mg coenzyme Q-10;
  d) from about 6 mg to about 45 mg alpha lipoic acid; and
  e) from about 2.5 mg to about 20 mg bromelain.

In still another case, a daily dosage of the dietary supplement composition can contain the following:
  a) from about 1400 mg to about 2800 mg phytosterols;
  b) from about 300 mg to about 800 mg omega-3 fatty acids;
  c) from about 20 mg to about 40 mg coenzyme Q-10;
  d) from about 20 mg to about 36 mg alpha lipoic acid; and
  e) from about 8 mg to about 15 mg bromelain.

In some cases, a daily dosage of the dietary supplement composition can contain the following:
  a) from about 1000 mg to about 3000 mg phytosterols
  b) from about 500 mg to about 1500 mg omega-3 fatty acids;
  c) from about 15 mg to about 45 mg coenzyme Q-10;
  d) from about 15 mg to about 45 mg alpha lipoic acid; and
  e) from about 2.5 mg to about 20 mg bromelain.

The phrase "daily dose" as used herein refers to the amount of active ingredient administered over a 24 hour period. A daily dose may be prepared and administered in the form of one or more tablets (e.g., two tablets, three tablets, four tablets, five tablets, and six tablets). In some cases, the one or more tablets can be administered in one or more dosages over the course of 24 hours (e.g., one dose, two doses, three doses, four doses, five doses, and six doses), wherein the one or more dosages do not exceed the total daily dose.

In some cases, when a daily dose is prepared for administration as a single tablet per day, the tablet can contain the following:
  a) about 2000 mg phytosterols;
  b) about 1000 mg omega-3 fatty acids;
  c) about 30 mg coenzyme Q-10; and
  d) about 30 mg alpha lipoic acid.

In other cases, when a daily dose is prepared for administration as two tablets per day, each tablet can contain the following:
  a) about 1000 mg phytosterols;
  b) about 500 mg omega-3 fatty acids;
  c) about 15 mg coenzyme Q-10; and
  d) about 15 mg alpha lipoic acid.

In another case, when a daily dose is prepared for administration as four tablets per day, each tablet can contain the following:
  a) about 500 mg phytosterols;
  b) about 250 mg omega-3 fatty acids;
  c) about 7.5 mg coenzyme Q-10; and
  d) about 7.5 mg alpha lipoic acid.

Optional Ingredients and Formulation

Compositions described herein can contain additional optional ingredients. For example, optional coloring and/or flavoring agents, e.g., to reduce the odor associated with fish oil and fish oil components, can be included. In addition, the compositions can contain a pharmaceutically acceptable carrier for in vivo administration to a mammal, including, without limitation, preservatives and other additives such as, for example, botanical extracts.

Compositions provided herein can be formulated as nutritional supplements, e.g., as liquids or capsules for oral ingestion. Capsules can be hard-shell or soft gel capsules.

The compositions provided herein can be ingested (e.g., orally or intragastrically). The route of administration can depend on a variety of factors, such as the health of the patient and the therapeutic goals. One method of administration is orally in the form of capsules at daily-recommended dosages. Capsules are provided in sizes that are acceptable for the consumer to swallow. For example, capsules can be in the range from about 250 mg to 3 g in size, or any size therebetween (e.g., 275 mg, 300 mg, 350 mg, 400 mg, 450 mg, 475 mg, 490 mg, 500 mg, 550 mg, 575 mg, 600 mg, 650 mg, 675 mg, 700 mg, 750 mg, 800 mg, 900 mg, 1000 mg, 1250 mg, 1500 mg, 1750 mg, 1800 mg, 1900 mg, 2 g, 2.1 g, 2.2 g, 2.3 g, 2.4 g, 2.5 g, 2.6 g, 2.7 g, 2.8 g, or 2.9 g).

A composition provided herein can be provided in the form of a gel cap, soft gelatin capsule (e.g., soft gel capsule), or hard gelatin capsule. For example, a composition described herein can be encapsulated by a hard gel capsule. For oral administration, soft gel capsules can be prepared by conventional means with pharmaceutically acceptable excipients such as binding agents, fillers, lubricants, disintegrants, or wetting agents. Soft gel capsule manufacturing methods are described in, e.g., U.S. Pat. No. 6,333,047.

The compositions provided herein can be formulated as capsules that can demonstrate improved shelf life, homogeneity, and product stability. Compositions can be designed to contain fillers such as beeswax, carnauba wax, and other polymeric media to mask any separation of formulations, e.g., in soft gel capsules. The addition of such fillers can require the use of larger capsules or an increase in dose to obtain therapeutic (e.g., effective) levels of active ingredients.

A composition incorporating a small carboxylic acid ester can be more stable than a composition lacking a small carboxylic acid ester in that (1) the composition is miscible and (2) the composition does not separate into separate phases in less than 24 hours, or less than 1 week, or less than 1 month. A small carboxylic acid ester can be present in an amount of less than about 5% by weight of the composition, or less than about 2% by weight, or less than about 1% by weight, to stabilize (or to improve the stability of) a composition described herein. Particularly useful carboxylic acid esters include, without limitation, triethyl citrate, diethyl maleate, and diethyl L-tartrate.

The compositions provided herein can be designed to contain a surfactant that wets, solubilizes, and/or emulsifies lipophilic components such as sterol compounds (e.g., phytosterol compounds) and/or fatty acid compounds (e.g., fish oil components and ω-3 fatty acids such as EPA or DHA). Typically, a surfactant is a food grade surfactant. A surfactant can be anionic, cationic, zwitterionic, or non-ionic. In certain embodiments, a surfactant can have a surface tension below 70 dyne/cm2, or below 40 dyne/cm2. A surfactant can have a hydrophilic/lipophilic balance of less than 20, or less than 10. See, e.g., Surfactants in Chemistry, J. Falbe, Ed., Springer-Verlag (1989), pp: 149-152.

One or more surfactants can be used in any combination or relative ratio. Examples of surfactants include, without limitation, alkanoylglycerides, monoacylglycerides, or monoglycerides (e.g., from rapeseed, canola, and cottonseed oils); propylene glycol monoesters (e.g., propylene glycol monostearate); lactoylesters; stearic acid; sodium stearoyl lactylate; ethoxylated alcohols; ethoxylated fatty esters and fatty esters; ethyoxylated glycerol esters; phosphorous organic derivatives such as dodecyl phosphonic acid, dodecyl phosphate, decylphosphonic acid, decyl phosphate, dioctylphosphate, myristearylphosphonic acid, lecithin and lecithin derivatives; sorbitan derivatives such as polyoxyethylene sorbitan monolaurate, sorbitan oleate, sorbitan laurate, sorbitan palmitate, sorbitan stearate, sorbitan myristearate, sorbitan ricinoleate, sorbitan linoleneate, and sorbitan linoleate; stearoyl-2-lactylates of sodium or calcium; sucrose and glucose esters and derivatives thereof; sulfosuccinates and derivatives; and mixtures of any of the above. Sorbitan derivatives and phosphorous organic derivatives, such as lecithin, can be used as surfactants to increase stability of a composition, particularly a composition formulated as a soft gel cap or hard shell caplet, or to increase bioavailability of a sterol compound (e.g., a phytosterol compound) and/or a fatty acid compound (e.g., a ω-3 fatty acid compound).

Surfactants can be obtained commercially as described elsewhere ("McCutcheon's Emulsifiers and Detergents," Int'l Ed. (2001), The Manufacturing Confectioner Publishing Co., NJ, USA). A surfactant can be less than 10% by weight of the composition, or less than 5%, or less than 2%.

Dietary supplement compositions according to the invention can be provided in any suitable dosage form, the selection and implementation of which will be apparent to those skilled in the art in view of the disclosure herein. Examples of such dosage forms include: a liquid, a gel, a tablet, a capsule, a powder, a confectionary, a shake, a bar, and a supplemented food. The selection and use of suitable excipients, flavorings, colorants, and the like will be apparent to those skilled in the art in view of the disclosure herein.

Further details on the use of sterols and fatty acid compounds in dietary supplements can be found U.S. Patent Publication No. 20050032757, entitled "Nutritional Supplements" and published Feb. 10, 2005, which is incorporated herein by reference in its entirety. All other references and patents referenced herein also expressly incorporated herein by reference in their entireties.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A dietary supplement consisting of:
    a) about 2000 mg phytosterols;
    b) about 1000 mg omega-3 fatty acids;
    c) bromelain;
    d) triethyl citrate, wherein the triethyl citrate is present in an amount less than about 1% by weight of the dietary supplement;
    e) one or more surfactants, wherein the one or more surfactants are present in an amount less than 10% by weight of the dietary supplement;
    f) about 30 mg coenzyme Q-10;
    g) about 30 mg alpha lipoic acid;
    h) ascorbic acid;
    i) alpha tocopherol;
    j) one or more excipients; and
    k) one or more flavoring agents,
    wherein the dietary supplement is in the form of two or more capsules or tablets.

2. The dietary supplement of claim 1, wherein the supplement is in the form of four or more capsules or tablets.

3. The dietary supplement of claim 2, wherein the supplement comprises four soft gelatin capsules.

4. The dietary supplement of claim 1, wherein the supplement is in the form of two or more capsules, and wherein each capsule is a gel cap, a soft gelatin capsule, or a hard gelatin capsule.

5. The dietary supplement of claim 1, wherein the phytosterols comprise a phytosterol ester selected from the group consisting of beta-sitosterol laurate ester, alpha-sitosterol laurate ester, gamma-sitosterol laurate ester, campesterol myristearate ester, stigmasterol oleate ester, campesterol stearate ester, beta-sitosterol oleate ester, beta-sitosterol palmitate ester, beta-sitosterol linoleate ester, alpha-sitosterol oleate ester, gamma-sitosterol oleate ester, beta-sitosterol myristearate ester, beta-sitosterol ricinoleate ester, campesterol laurate ester, campesterol ricinoleate ester, campesterol oleate ester, campesterol linoleate ester, stigmasterol linoleate ester, stigmasterol laurate ester, stigmasterol caprate ester, alpha-sitosterol stearate ester, gamma-sitosterol stearate ester, alpha-sitosterol myristearate ester, gamma-sitosterol palmitate ester, campesterol ricinoleate ester, stigmasterol ricinoleate ester, campesterol ricinoleate ester, beta-sitosterol, alpha-sitosterol, gamma-sitosterol, campesterol, stigmasterol, stigmasterol stearate ester, and combinations thereof.

6. The dietary supplement of claim 1, wherein the omega-3 fatty acids are included as a fish oil comprising about 30-33% eicosapentaenoic acid (EPA) and about 20-22% docosahexaenoic acid (DHA).

7. The dietary supplement of claim 1, wherein the omega-3 fatty acids are selected from the group consisting of EPA and derivatives thereof, and DHA and derivatives thereof.

8. The dietary supplement of claim 1, wherein the one or more surfactants comprise sorbitan oleate and lecithin.

9. A dietary supplement consisting of:
    a) about 500 mg phytosterols;
    b) about 250 mg omega-3 fatty acids;
    c) bromelain;
    d) triethyl citrate, wherein the triethyl citrate is present in an amount less than about 1% by weight of the dietary supplement;
    e) one or more surfactants, wherein the one or more surfactants are present in an amount less than 10% by weight of the dietary supplement;
    f) about 7.5 mg coenzyme Q-10;

g) about 7.5 mg alpha lipoic acid;
h) ascorbic acid;
i) alpha tocopherol;
j) one or more excipients; and
k) one or more flavoring agents.

10. The dietary supplement of claim 9, wherein the supplement is in the form of a soft gelatin capsule.

11. The dietary supplement of claim 9, wherein the one or more surfactants comprise sorbitan oleate and lecithin.

12. The dietary supplement of claim 9, wherein said supplement comprises about 0.1% by weight bromelain.

13. A method comprising administering to a mammal a dietary supplement, the dietary supplement consisting of:
   a) about 2000 mg phytosterols;
   b) about 1000 mg omega-3 fatty acids;
   c) bromelain;
   d) triethyl citrate, wherein the triethyl citrate is present in an amount less than about 1% by weight of the dietary supplement;
   e) one or more surfactants, wherein the one or more surfactants are present in an amount less than 10% by weight of the dietary supplement;
   f) about 30 mg coenzyme Q-10;
   g) about 30 mg alpha lipoic acid;
   h) ascorbic acid;
   i) alpha tocopherol;
   j) one or more excipients; and
   k) one or more flavoring agents,
   wherein the dietary supplement is provided as two or more capsules or tablets.

14. The method of claim 13, wherein the supplement is provided as four or more capsules or tablets.

15. The method of claim 13, wherein the supplement is provided as two or more capsules, and wherein each capsule is a gel cap, a soft gelatin capsule, or a hard gelatin capsule.

16. The method of claim 13, wherein the supplement is provided as four soft gelatin capsules, and wherein the administering occurs over the course of a 24 hour period.

* * * * *